US010183178B2

(12) United States Patent
Boisseau et al.

(10) Patent No.: US 10,183,178 B2
(45) Date of Patent: Jan. 22, 2019

(54) METHOD AND APPARATUS FOR CONTROLLED PENCIL BEAM THERAPY

(71) Applicant: Pyramid Technical Consultants Inc., Lexington, MA (US)

(72) Inventors: Raymond Paul Boisseau, Waltham, MA (US); John Gordon, Henfield (GB); William P. Nett, Waltham, MA (US); Kan Ota, Bedford, MA (US)

(73) Assignee: Pyramid Technical Consultants Inc., Lexington, MA (US)

( * ) Notice: Subject to any disclaimer, the term of this patent is extended or adjusted under 35 U.S.C. 154(b) by 440 days.

(21) Appl. No.: 15/146,541

(22) Filed: May 4, 2016

(65) Prior Publication Data

US 2017/0319873 A1    Nov. 9, 2017

(51) Int. Cl.
*A61N 5/10* (2006.01)

(52) U.S. Cl.
CPC ......... *A61N 5/1067* (2013.01); *A61N 5/1043* (2013.01); *A61N 5/1048* (2013.01); *A61N 2005/1074* (2013.01); *A61N 2005/1087* (2013.01)

(58) Field of Classification Search
USPC .................................................. 250/396 ML
See application file for complete search history.

(56) References Cited

U.S. PATENT DOCUMENTS

| 7,829,866 | B2 * | 11/2010 | Purser | H01J 37/05 |
| | | | | 250/396 ML |
| 9,236,222 | B2 * | 1/2016 | Yagita | H01J 37/3171 |
| 9,984,863 | B2 * | 5/2018 | Verenchikov | H01J 49/403 |

* cited by examiner

*Primary Examiner* — Phillip A Johnston (74) *Attorney, Agent, or Firm* — Intrinsic Law Corp.

(57) ABSTRACT

A control system for providing a closed loop, real time control of a charged particle pencil beam is disclosed. The system includes a first detector apparatus, a second detector apparatus, a first orthogonal magnetic deflector apparatus, a second orthogonal magnetic deflector apparatus, and a controller. The controller compares the measured position and beam angle of the beam with a model position and beam angle of a model beam to determine an offset error and a beam angle error. The first orthogonal magnetic deflector apparatus includes a pair of electromagnets to correct a first component of the offset and beam angle errors. The second orthogonal magnetic deflector apparatus includes a pair of electromagnets to correct a second component of the offset and beam angle errors. The beam can be iteratively adjusted during patient therapy or short pauses in patient therapy.

20 Claims, 9 Drawing Sheets

METHOD AND APPARATUS FOR CONTROLLED PENCIL BEAM THERAPY

TECHNICAL FIELD

The present application generally relates to controlling pencil beam treatments and treatment systems for example in the context of proton beam therapy.

BACKGROUND

Charged particle therapy is used to treat certain conditions (e.g., cancer) in patients using focused, collimated or other spatially limited energetic particle beams. The principle generally relies on the controlled and localized deposition of sufficient energy in a treatment volume. The treatment volume may be an arbitrary three-dimensional volume (e.g., a cancer tumor) within the patient's body. In some instances, ionizing radiation is used to physically overcome the diseased tissue's survival thresholds and thereby destroy the diseased tissue.

In all such therapy procedures it is important to control the amount and location of the applied therapy beams and fields applied to a patient's body to avoid or minimize harm to healthy tissues and organs in the vicinity of the diseased volume. Surgical planning routines, sometimes employing medical imaging to guide the therapy procedure, are used to define the treatment volume and to prescribe the application of the therapy to the treatment volume. Time-dependent modeling, monitoring and other controls are employed to safely carry out proton therapy and similar treatments because the energy beams used in the treatments can accidentally injure the patients if applied incorrectly.

Pencil beam proton and other light ion therapy is used because of its ability to deliver dose to the patient with greatly improved spatial resolution and accuracy. It employs relatively narrow cross-sectional beams of protons, which can be on the order of a few millimeters in diameter. The advantages of the method require that the proton beam is positioned with a high degree of precision.

Figure 1:
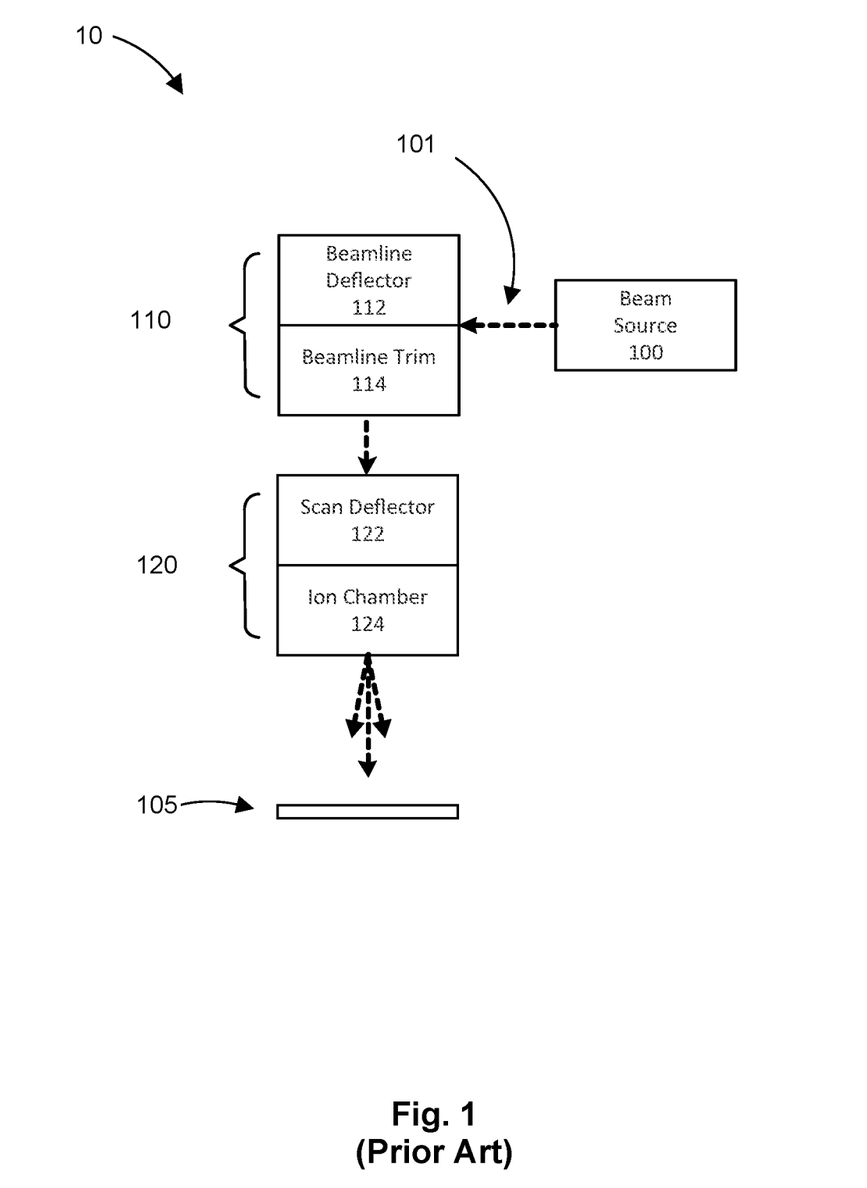
FIG. 1 illustrates a basic proton therapy system according to the prior art.

FIG. 1 illustrates a basic light ion therapy system such as a pencil beam proton therapy system (PBS) 10. Current proton therapy systems 10 include a proton beam source 100, which can generate a directed beam of ionizing radiation 102 at a desired energy level (typically 30 to 250 MeV). The beam 101 is transported from the source to the scanning system 120 ("Nozzle") and deflected as needed using one or more primary bending electromagnets 112, fine trim electromagnets 114 or other components in beamline 110, as well as scanner deflectors 122 in scan nozzle 120. An ion chamber (sometimes "IC") 124 is disposed before the target of the beam. The target is supposed to be at a location in a patient, but it is characterized for control purposes by its projection onto the nominal "isocenter" plane 105. The resulting beam reaching the patient may be deflected, intentionally or unintentionally, scanned or otherwise controlled by factors causing its beam angle and position in three dimensional space to be altered over time. Those practiced in the art have also recognized that the beam tends to deviate from its commanded position between treatment sessions and during treatments according to unwanted variation in magnetic fields and other factors affecting the beam's spatial positioning. These variations are generally imposed onto a series of commanded positions, and can potentially adversely affect the continued accuracy and effectiveness of the treatment by negatively affecting healthy organs in the vicinity of the diseased treatment volume.

If a beam has moved away from its desired trajectory by a clinically unacceptable amount, the beam must be stopped and therapeutic treatment halted. Appropriate adjustments can be made to the system to correct the offset of the beam based on the last measured position error.

Such a process of error correction increases the time for treatment, leading to increased expense. It also requires operator intervention, with an associated possibility of operator error. Extended treatment time may also introduce errors due to patient movement and associated deviations between the actual patient position and diagnostic imaging data. However, error correction may not be possible if the error is too large or if the error cannot be corrected quickly, in which case patient irradiation is abandoned.

Moreover, it is generally not acceptable to retune the beam if such retuning includes the beam reaching the patient as this could compromise the intended dose distribution for the patient in a way that is not correctable.

What is needed is an apparatus and method for maintaining beam alignment without impacting patient treatment.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to a system for providing real-time trajectory correction of a charged particle beam. The system includes a particle beam generator to generate a generated particle beam parallel to a reference axis. The system also includes a transport beamline apparatus comprising beamline deflector magnets to generate magnetic fields to deflect said generated particle beam along a defined trajectory towards a scan nozzle. The system also includes a scan nozzle comprising at least one scan magnet to direct said deflected particle beam to a target position in a patient. The system also includes a first detector apparatus disposed between said transport beam apparatus and said scan nozzle, said first detector apparatus configured to output a first signal representing a first measured position of said deflected particle beam in orthogonal first and second planes, wherein said reference axis lies on said first and second planes. The system also includes a second detector apparatus disposed between said first detector apparatus and said scan nozzle, said second detector apparatus configured to output a second signal representing a second measured position of said deflected particle beam in said first and second planes. The system also includes a pair of first correction magnets disposed between said first detector apparatus and said particle beam generator, said first correction magnets configured to (a) receive from a control system an offset control signal and a beam angle control signal and (b) generate magnetic fields to correct a measured offset error and a measured beam angle error with respect to said first plane. The system also includes a pair of second correction magnets disposed between said first detector apparatus and said particle beam generator, said second correction magnets configured to (a) receive from said control system an offset control signal and a beam angle control signal and (b) generate magnetic fields to correct said measured offset error and said measured beam angle error with respect to said second plane. The control system comprises a processor, said control system configured to: receive as inputs said first and second signals; calculate a measured trajectory of said deflected particle beam based on said first and second measured positions, said measured trajectory including a measured beam angle and a measured offset; determine said measured beam angle error based on said measured beam angle and a model beam angle of said generated particle beam; determine said measured offset error based on (a) at least one of said measured offset, said first measured position, or said second measured position and (b) a corresponding model position of said generated particle beam; generate said beam angle control signal based on said measured beam angle error; and generate said offset control signal based on said measured offset error.

Another aspect of the invention is directed to a system for providing real-time trajectory correction of a charged particle beam. The system includes a particle beam generator to generate a generated particle beam parallel to a reference axis. The system also includes a transport beamline apparatus comprising beamline deflector magnets to generate magnetic fields to deflect said generated particle beam along a defined trajectory towards a scan nozzle. The system also includes a scan nozzle comprising at least one scan magnet to direct said deflected particle beam to a target position in a patient. The system also includes a detector apparatus disposed between said transport beam apparatus and said scan nozzle, said detector apparatus configured to output a measured position signal representing a first measured position of said deflected particle beam in orthogonal first and second planes, wherein said reference axis lies on said first and second planes. The system also includes a correction electromagnet apparatus disposed between said detector apparatus and said particle beam generator, said correction electromagnetic apparatus configured to (a) receive from a control system an offset control signal and (b) generate magnetic fields to correct a measured offset error. The said control system comprises a processor, said control system configured to receive as an inputs said measured position signal; determine said measured offset error based on said first measured position and a model position of said generated particle beam; and generate said offset control signal based on said measured offset error.

IN THE DRAWINGS

For a fuller understanding of the nature and advantages of the present invention, reference is made to the following detailed description of preferred embodiments and in connection with the accompanying drawings, in which.

DETAILED DESCRIPTION

Aspects of this disclosure are directed to a novel closed loop control system for a charged particle pencil beam system (PBS). The control system can be used in real time during therapy or during short breaks in therapy without removing the patient from the therapy position. Thus, the control system reduces system downtime needed to align a PBS delivery system during patient treatment This disclosure recognizes that trajectory correction requires in general the ability to control 4 independent parameters. The control system provides control over the offset of the beam and the beam angle of the beam in two planes. The offset of the beam includes a first component with respect to a first plane (e.g., an "x" component with respect to the x-z plane) and a second component with respect to a second plane (e.g., a "y" component with respect to the y-z plane). Similarly, the beam angle includes a first component with respect to a first plane (e.g., an "x" component with respect to the x-z plane) and a second component with respect to a second plane (e.g., a "y" component with respect to the y-z plane). The "x" and "y" components can be considered independently controlled in many embodiments. For example, these degrees of freedom can be independently controlled in combined function systems having dipole, quadrupole, sextupole, and/or octopole electromagnets which can behave like two independent transport systems (e.g., in the "x" direction and the "y" direction). This task is simplified if done in the last section of the beamline, which is typically a linear arrangement of magnetic (e.g., electromagnetic) elements.

In general, the control system includes two beam detectors with two-dimensional position capability and either two pairs of orthogonal correctional electromagnets, one pair of combined function correctional electromagnets, or a combination thereof (e.g., one pair of orthogonal correctional electromagnets and one combined function correctional electromagnet). Using the beam detectors, the control system determines the measured offset and measured beam angle of the beam with respect to first and second planes (e.g., x-z and y-z planes). The control system compares the measured offset and measured beam angle with the model offset and model beam angle to determine an offset error and a beam angle error in each plane. Each pair of orthogonal correctional electromagnets operates to reduce the offset and beam angle errors with respect to a given plane (e.g., x-z or y-z plane). Each pair of correctional magnets deflect the beam by correcting the offset (in the given plane) in the first "leg" and then correcting the beam angle (in the same given plane) in the second "leg." In some embodiments, one, some, or all of the correctional magnets are electromagnets, which allow the respective magnetic fields generated by the electromagnets to be controlled electronically.

Embodiments of the disclosure are directed to a system for providing real-time trajectory correction of a charged particle beam. Error in the trajectory can be resolved into errors in two directions orthogonal to the nominal trajectory of the beam, usually labeled x and y axes, with the z axis being along the nominal trajectory. Measurement and control of the trajectory in these two orthogonal directions can be done independently. The system can include a particle beam generator to generate a particle beam with a trajectory close to close to a nominal axis. The system also includes a transport beamline apparatus comprising a series of electromagnets used to deliver the beam to the scan nozzle, the number and design of these magnets being sufficient to allow the beam to be brought to a trajectory precisely or closely aligned with the nominal entry axis ("reference axis") into the scan nozzle, given the correct magnet settings. The system also includes a scan nozzle comprising a scan magnet system to direct the particle beam to any target position in a patient.

Considering a first error the beam in an x direction orthogonal to the reference axis, the system also includes a first x axis detector disposed between said transport beam apparatus and said scan nozzle, the first x axis detector configured to output a first signal representing a first measured x position of said deflected particle beam along a first x axis perpendicular to the reference axis. The system also includes a second x axis detector disposed between said first detector and said scan nozzle, the second x axis detector configured to output a second signal representing a second measured x position of the deflected particle beam along a second x axis perpendicular to said reference axis. The offset and angle of the beam trajectory projected onto the x-z plane can be determined from this information. The system also includes a first x correction magnet and second x correction magnet for correction in the x-z plane, the first and second x correction magnets disposed between the particle beam generator and the first detector, the first and second x correction magnets configured to (a) receive an angular deflection control signal and (b) generate magnetic fields to adjust the deflected beam angle in x-z plane.

Considering a second error in the beam in a y direction orthogonal to the reference axis and to the x direction, the system also includes a first y axis detector disposed between the transport beam apparatus and the scan nozzle, the first y axis detector configured to output a first signal representing a first measured y position of the deflected particle beam along a y axis perpendicular to the reference axis. The system also includes a second y axis detector disposed between the first y axis detector and the scan nozzle, the second y axis detector configured to output a second signal representing a second measured y position of the deflected particle beam along a y axis perpendicular to said reference axis. If the path between the first and second detectors is straight, then first and second y axes will be mutually parallel and orthogonal to said x axes. The offset and angle of the beam trajectory projected onto the y-z plane can be determined from this information. The system also includes a pair of second correction magnets for correction in the y-z plane disposed between said particle beam generator and said first y axis detector, the second correction magnets configured to (a) receive an angular deflection control signal and (b) generate magnetic fields to adjust said deflected beam angle in y-z plane.

Detectors for x and y measurements may be conveniently combined into detectors simultaneously sensitive in both axes in order to save space along the beam axis. Thus there would be one first detector sensitive to both x and y position and one second detector sensitive to both x and y position. An example of such a combined detector is a pixelated detector.

Correction magnets in x and y directions may be conveniently combined in "combined function" electromagnets that can deflect simultaneously in orthogonal axes in order to save space along the beam axis. Thus there would be one first combined function correction electromagnet capable of deflecting in both x and y directions and one second combined function correction electromagnet capable of deflecting in both x and y directions. An example of a combined function magnet is a multipole electromagnet.

Although the most general correction uses two detector points and four control points to generate a full trajectory correction, a simplified system may use only a single detector point and two control points (e.g., correction electromagnets) to correct only an offset correction in x and y.

Although the x and y scan magnets are considered part of the scan nozzle, one implementation utilizes the scan magnets as two of the control points.

The system also includes a control system comprising a processor. The control system is configured to receive as inputs said first and second signals for each of x and y axis. The control system calculates for each of x and y axis a measured trajectory of said deflected particle beam based on said first and second measured positions, said measured trajectories including a measured beam angle and a measured offset. The control system also determines a measured beam angle error based on said measured beam angle and a model beam angle of said generated particle beam; determines a measured offset error based on (a) at least one of said measured offset, said first measured position, or said second measured position and (b) a model position of said generated particle beam; generates said beam angle control signal based on said measured beam angle error; and generates said offset control signal based on said measured offset error.

One or more embodiments or implementations are hereinafter described in conjunction with the drawings, where like reference numerals are used to refer to like elements throughout, and where the various features are not necessarily drawn to scale.

Figure 2:
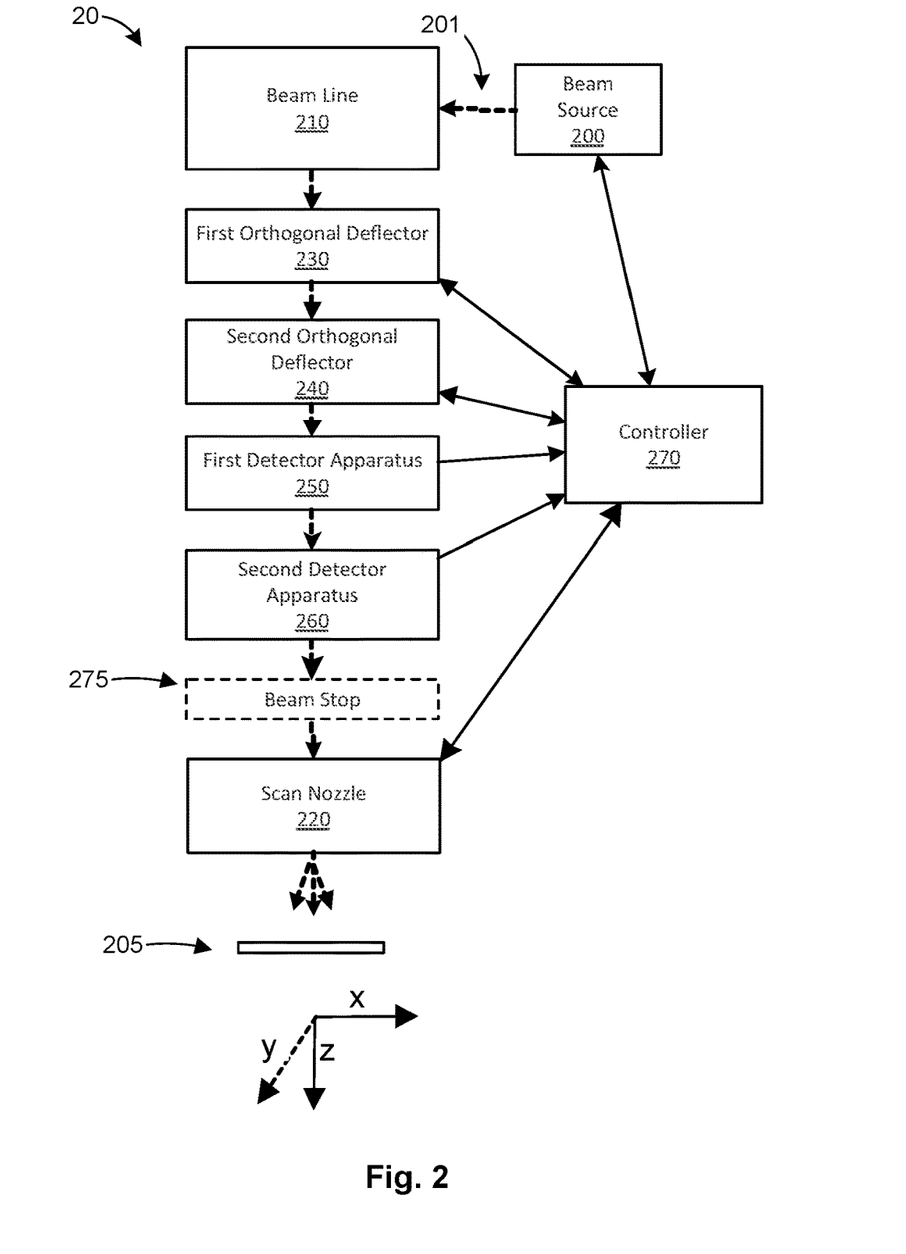
FIG. 2 illustrates a pencil beam system according to an embodiment.

FIG. 2 illustrates a PBS system 20 according to an embodiment. The system 20 includes beam source 200, beamline 210, scan nozzle 220, first orthogonal deflector apparatus 230, second orthogonal deflector apparatus 240, first detector apparatus 250, second detector apparatus 260, and controller 270. Beam source 200, beamline 210, and scan nozzle 220 can be the same as respective beam source 100, beamline 110, and scan nozzle 120 described above. First detector apparatus 250 includes one or more IC detectors to measure the two-dimensional position of beam 201 at a first location. For example, first detector apparatus 250 can include a first strip detector for measuring the position of charged particle pencil beam 201 along a first axis (e.g., the "x" axis) orthogonal to the direction of travel (e.g., the "z" axis") of beam 201 and a second strip detector for measuring the position of beam 201 along a second axis (e.g., the "y" axis) orthogonal to the direction of travel of beam 201. Such strip detectors include a plurality of parallel rows of electrodes that can detect the position of the beam in direction orthogonal to the rows. For example, a strip detector having vertical rows of electrodes (e.g., along the "y" axis") can detect the position of the beam in the horizontal direction (e.g., along the "x" axis). In some embodiments, the "x" axis corresponds to the bending direction of local dipole magnets. The "y" axis can be orthogonal to the "x" axis.

Such strip detectors are preferably thin to minimize scatter, energy degradation, and/or distortion of beam 201. An example of such a strip detector can be found in U.S. patent application Ser. No. 14/215,311, entitled "Method and Apparatus for Monitoring a Charged Particle Beam,"

which is hereby incorporated by reference. Alternatively, first detector apparatus 250 can include a thin pixelated detector that includes a grid of detector elements to measure the position of beam 201 in a given plane (e.g., in the x-y plane, which is orthogonal to the z axis). An example of such a pixelated detector can be found in U.S. patent application Ser. No. 14/493,098, entitled "Method and System for Measuring, Verifying, and Displaying Progress of Dose Delivery in Scanned Beam Particle Therapy," which is hereby incorporated by reference. The '311 and the '098 applications are assigned to the same assignee as this application.

Second detector apparatus 260 can be the same or different than first detector apparatus 250. For example, each detector apparatus 250, 260 can include a pixelated detector or a pair of strip detectors. Similarly, detector apparatus 250 can include a pixelated detector and detector apparatus 260 can include a pair of strip detectors (or vice versa).

Each detector apparatus 250, 260 outputs a signal that represents the two-dimensional position of beam 201. The signal is transmitted through high-speed readout electronics at a data rate that allows the controller 270 to react in a time comparable to the system response time (e.g., about 1 millisecond) to minimize any error in patient dosage. The controller 270 then determines the position (i.e., centroid) of the beam based on the data (e.g., intensity distribution) provided in the signal. When a detector apparatus 250/260 includes a pair of strip detectors, the controller 270 calculates the position (x, y) measured by each strip detector. Thus, the controller 270 calculates an "x" position and a "y" position of beam 201 at the location of each detector apparatus 250, 260.

Using the position of beam 201 at each detector apparatus 250, 260, and the distance between corresponding detectors, the controller 270 calculates the beam angle of beam 201. The beam angle includes an "x" component and a "y" component, which correspond to beam angles $\Theta$ and $\phi$, respectively, measured with respect to the direction of travel of beam 201 as it leaves beam line 210, which is parallel to the z axis. The controller 270 compares the measured beam angles $\Theta$(measured) and $\phi$(measured) with model beam angles $\Theta$(model) and $\phi$(model) to determine beam angle errors $\Delta\Theta$ and $\Delta\phi$.

If strip detectors are used as detector apparatus 250, 260, the beam angle is determined using the distance between the corresponding strip detectors that measure the position of the beam along the same axis (e.g., the strip detector at each location that measures the position along the "x" axis). Similarly, if the first detector apparatus 250 includes a pixelated detector and the second detector apparatus 260 includes a pair of strip detectors, the relevant distance is the distance between the pixelated detector and the strip detector that measured the given component (e.g., "y" position) of beam 201 to determine the "y" component of the beam angle.

In general, the measured beam angles $\Theta$(measured) and $\phi$(measured) are determined as follows:

$$\Theta = \tan^{-1}\frac{x2 - x1}{d\_x} \text{ and } \Phi = \tan^{-1}\frac{y2 - y1}{d\_y}$$

where d_x and d_y are the respective distances between the relevant first and second detector apparatus 250, 260. For example, d_x is the distance between the detectors (strip and/or pixelated detectors) that measured the "x" position of beam 201.

In addition, controller 270 determines an offset error in the measured position of beam 201. The offset error can be determined by comparing the measured position of beam 201 with a model position of beam 201. Since the position of the beam 201 includes an "x" component and a "y" component, the offset errors are $\Delta x$ and $\Delta y$. The measured and model positions can be with respect to either detector apparatus 250, 260.

The values of $\Delta\Theta$, $\Delta\phi$, $\Delta x$, and $\Delta y$ are used by the controller to calculate new values of the four control signals based on direct calculation, an iterative control algorithm, such as a PI, PID, or other control algorithm as known in the art. The control signals are sent to first and second orthogonal deflector apparatus 230, 240 as discussed below. In some embodiments, the errors are corrected iteratively. As further described below, the first and second orthogonal deflector apparatus 230, 240 can each include a pair of magnets (e.g., electromagnets) to reduce the offset and beam angle errors in a given plane. For example, orthogonal deflector apparatus 230 can include a pair of magnets to reduce the "x" component of the offset $\Delta x$ and beam angle $\Delta\Theta$ errors. In another example, orthogonal deflector apparatus 240 can include a pair of magnets to reduce the "y" component of the offset $\Delta y$ and beam angle $\Delta\phi$ errors.

In some embodiments, first and/or second orthogonal deflector apparatus 230, 240 can be disposed between beam source 200 and beam line 210.

Since the detectors in detector apparatus 250, 260 have minimal beam scatter and degradation, the system 20 can be used when a patient is at isocenter 205, for example during therapeutic treatment. Thus the system 20 provides a closed loop, real time or substantially real time correction/calibration of charged particle pencil beam 201, which greatly reduces system downtime and greatly improves patient throughput.

In some embodiments, an optional beam stop 275 is disposed between second detector apparatus 260 and scan nozzle 220. The beam stop 275 can be configured to block beam 201 during any correction that might require an extended period of time to execute. The beam stop 275 can block the beam 201 from reaching the patient during retuning/calibration/setup, without having to move the patient, and allow beam 201 to pass (and reach the patient) when the retuning/calibration/setup is complete, for example to provide therapy to a patient. For example, beam stop 275 can be used when the energy of beam 201 is adjusted, which is particularly likely to introduce a beam angle error in some systems.

Beam stop 275 can be in a variety of forms, such as a cylinder or sphere with an aperture for allowing beam 201 to pass through in one orientation (e.g., when the aperture is in alignment with beam 201) and block beam 201 in other orientations (e.g., when the aperture is not in alignment with beam 201), for example by rotating the cylinder/sphere. Alternatively, beam stop 275 can be moved into and out of the path of beam 201. For example, beam stop 275 can be a solid object that moves orthogonally to the beam 201 in the "x" or "y" direction, like a swing or guillotine.

In some embodiments, beam stop 275 blocks beam 201 with a sufficiently short actuator time (100 msec or so) to allow for rapid sampling and adjustment of the beam's calibration settings during patient treatment.

Figure 3:
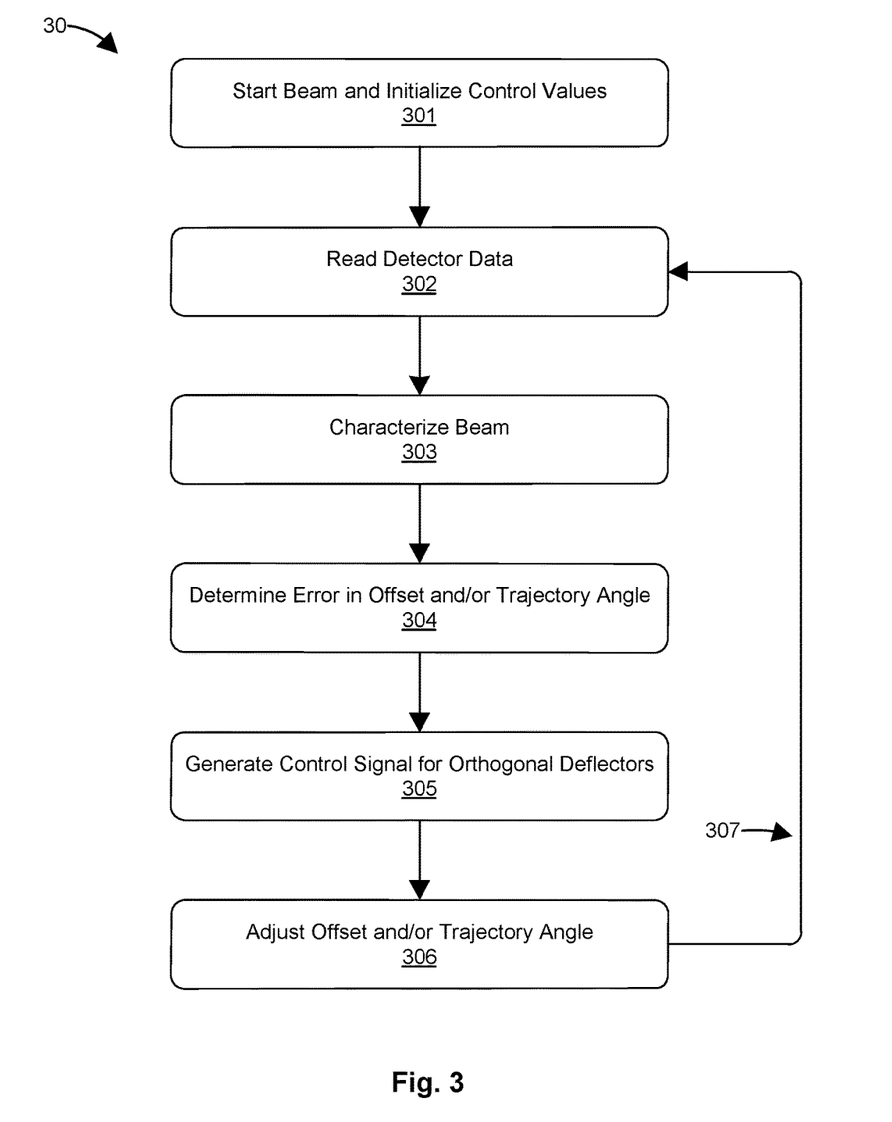
FIG. 3 is a flow chart illustrating a method for real-time trajectory correction of a charged particle pencil beam according to an embodiment.

FIG. 3 is a flow chart 30 illustrating a method for real-time trajectory correction of a charged particle pencil beam according to an embodiment. In step 301, the beam is generated at a desired offset, beam angle, and energy level. When the beam is first generated, the calibration and control parameters are initialized to zero as no correction control signals have been generated. Alternatively, the controller can generate initial control parameters for the beam based on historical data of control parameters used for the beam at the same energy level.

In step 302, the detector data output from first and second detector apparatus 250, 260 are read and collected through readout electronics. Readout electronics 340 have sufficient bandwidth and processing speed to collect data at about 1 kHz or more.

In step 303, the controller characterizes the beam based on the data output from detector apparatus 250, 260. The characterization includes calculating the measured centroid position of the beam at each detector apparatus, which includes x and y position components as discussed above. The characterization also includes calculating the measured beam angle of the beam based on the measured centroid positions and the distance between corresponding detectors. The measured beam angle is used to determine the measured beam angles $\Theta$(measured) and $\phi$(measured).

In step 304, the controller compares the characterized beam with a model beam to determine if any error correction is needed. The model beam has a model position or offset (x (model), y (model)) and a model beam angle, including model beam angles $\Theta$(model) and $\phi$(model). As discussed above, the error calculation of the beam position or offset can be made using one of the measured positions at detectors 250/260 or using the projected offset of the beam at the isocenter plane. The model offset position can be scaled or adjusted based on the measured or projected position used for comparison. In general, the beam error can be defined by the following equations:

$$\Delta\Theta = \Theta(\text{measured}) - \Theta(\text{model})$$

$$\Delta\phi = \phi(\text{measured}) - \phi(\text{model})$$

$$\Delta x = x(\text{measured or projected}) - x(\text{model})$$

$$\Delta y = y(\text{measured or projected}) - y(\text{model})$$

In step 305, the controller generates control signals to independently correct for the above errors in the parameters $\Theta$, $\phi$, x, and y. The control signal can be generated based on a control algorithm, such as PI or PID, as discussed above.

In step 306, the control signals are sent to first and second orthogonal deflector apparatus 230, 240. First orthogonal deflector apparatus 230 can include a pair of electromagnets to adjust the x offset and/or the x beam angle $\Theta$ based on the control signals for those parameters. Likewise, second orthogonal deflector apparatus 240 can include a pair of electromagnets to adjust the y offset and/or the y beam angle $\phi$ based on the control signals for those parameters. Electromagnets for first and second orthogonal deflector apparatus may be combined function magnets (e.g., multipole electromagnets) to reduce the total amount of space needed.

In some embodiments, the first orthogonal deflector apparatus 230 only adjusts the x offset and the second orthogonal deflector apparatus 240 only adjusts the y offset. Likewise, in some embodiments, the first orthogonal deflector apparatus 230 only adjusts the x beam angle $\Theta$ and the second orthogonal deflector apparatus 240 only adjusts the y beam angle $\phi$. Any combination of the above can also occur (e.g., the first orthogonal deflector apparatus 230 adjusts both the x offset and the x beam angle $\Theta$ while the second deflector apparatus 240 only adjusts the y beam angle y offset).

In step 307, the process returns to step 302 (read detector data) to characterize and adjust (if needed) the now-adjusted beam. Thus, the beam can be controlled in a closed loop and corrected iteratively and in real time. Since this process can occur without moving the patient, it can result in a significant savings in time and money, as discussed above.

In some embodiments, the beam adjustment parameters from each scan is stored in a memory. When the beam starts (step 301) and/or when the energy of the beam changes, the controller can use historical adjustment parameters (in the same scan run and/or over many scan runs over days, weeks, etc.) at the same energy level as the starting point for correcting the offset and/or beam angle of the beam. The historical adjustment parameters can provide a relatively good approximation for the necessary adjustment.

Figure 4:
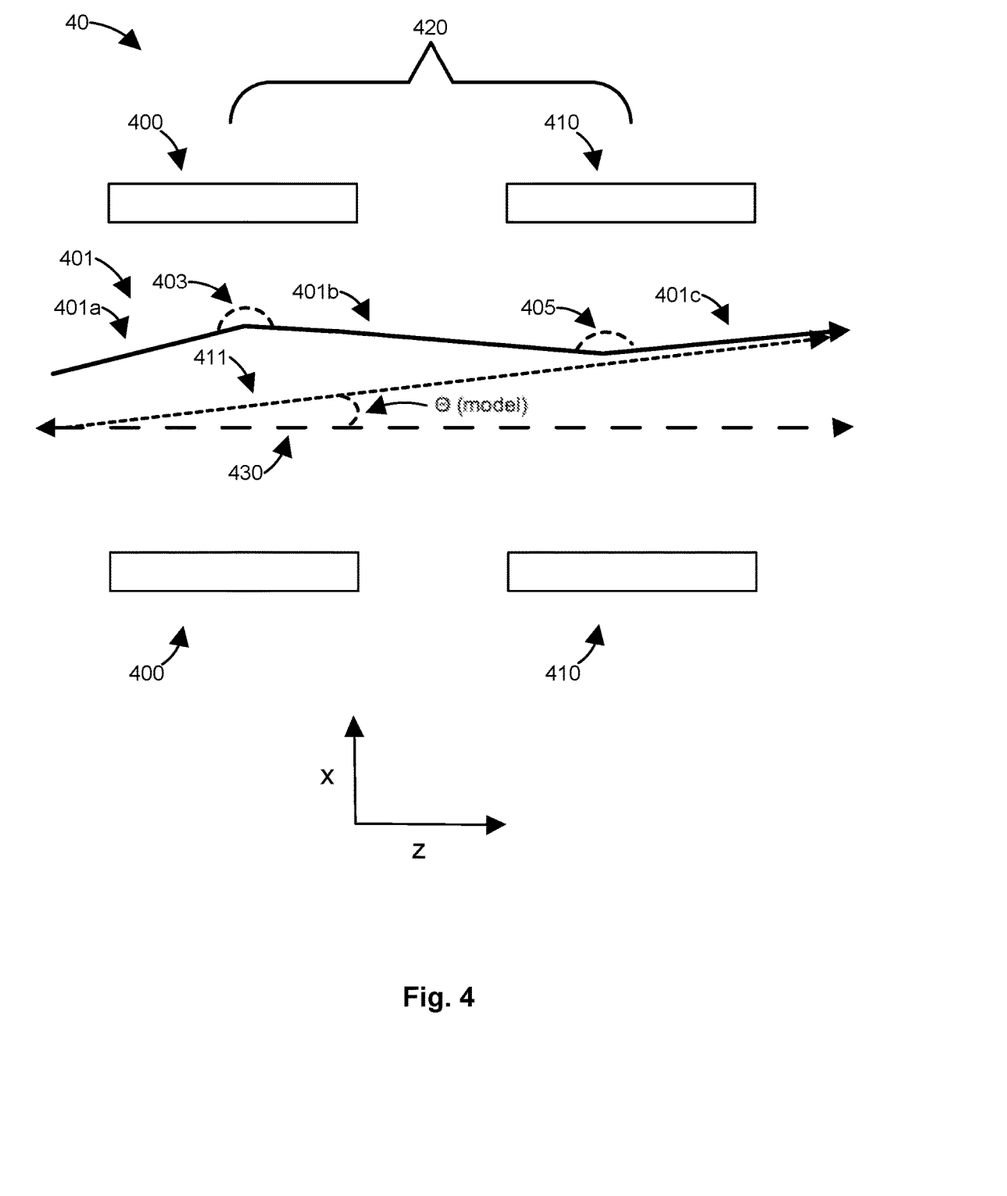
FIG. 4 is a side view of an orthogonal deflector apparatus according to an embodiment.

FIG. 4 is a side view of an orthogonal deflector apparatus 40 according to an embodiment. The orthogonal deflector apparatus 40 can be the same as first and/or second orthogonal deflector apparatus 230, 240, discussed above. The apparatus 40 includes first and second orthogonal deflector pairs 400, 410 separated by a distance 420, generally measured from the center of each deflector. The deflectors 400, 410 are configured to deflect the beam along a first axis (e.g., the x axis) orthogonal to an axis 430 parallel to the direction of travel of the beam (e.g., the z axis). The deflectors 400, 410 can provide a very good approximation of a discontinuous change in beam trajectory in the relevant axis (e.g., first axis) occurring at the longitudinal center (i.e., along the z axis) of each deflector magnet.

As illustrated, the first deflector pair 400 includes first opposing electromagnets that are aligned along a first axis parallel to the x axis. Similarly, the second deflector pair 410 includes second opposing electromagnets that are aligned along a second axis parallel to the x axis. The distance between the opposing electromagnets for each pair can be centered with respect to the nominal z axis.

In operation, the deflectors 400, 410 work together to adjust the x offset and/or the x beam angle $\Theta$ of beam 401. In some embodiments, the deflectors 400, 410 only need to deflect the beam by a few milliradians to correct the offset and beam angle. The first orthogonal deflector 400 receives a first control signal from controller 270 to adjust the x offset of beam 401a. In response to the first control signal, the first orthogonal deflector 400 generates a first magnetic field, orthogonal to the z axis, to deflect the beam laterally at a first beam angle 403. The first beam angle 403 is selected so that deflected beam 401b is at the model x offset of model beam 411 when the deflected beam 401b travels distance 420 to reach the second orthogonal deflector 410.

The second orthogonal deflector 410 receives a second control signal from controller 270 to adjust the beam angle $\Theta$ of beam 401. In response to the second control signal, the second orthogonal deflector 410 generates a second magnetic field, orthogonal to the z axis, to deflect the deflected beam 401b at a second beam angle 405. The second beam angle 405 is selected so that corrected beam 401c is at the model beam angle $\phi$(model) of model beam 411. The beam angles $\Theta$ and $\phi$ can be measured with respect to the z axis or a line parallel to the z axis.

Although deflectors 400 and 410 are each illustrated as having a pair of magnets, it is noted that other deflectors 400, 410 can have other configurations. For example, one or both deflectors 400, 410 can include a magnet in the shape of a toroid, annulus, or other shape as known in the art. In another example, deflectors 400, 410 can include quadrupole, sextupole, or octopole magnetic deflectors where two dipoles are effectively superimposed as a "combined function" electromagnet which can reduce the longitudinal footprint of the deflectors. An example of a sextupole and an octopole magnetic deflector can be found in U.S. Pat. No. 8,378,312, entitled "System, Apparatus and Method For Deflecting a Particle Beam," which is incorporated herein by reference. The '312 patent is assigned to the same assignee as this application.

As illustrated in FIG. 4, orthogonal deflector apparatus 40 is configured to correct the x offset and/or the x beam angle Θ of beam 401. However, it is noted that the configuration of orthogonal deflector apparatus 40 in FIG. 4 is exemplary and other configurations are possible. For example, orthogonal deflector apparatus 40 can be configured to adjust the y offset and/or the y beam angle φ of beam 401, or any other offset and/or beam angle depending on the relevant coordinate system. Accordingly, when orthogonal deflector apparatus 40 is configured to correct the x offset and/or the x beam angle Θ (i.e., in the exemplary embodiment illustrated in FIG. 4), orthogonal deflector apparatus 40 can be the same first orthogonal deflector apparatus 230 discussed above. Similarly, when orthogonal deflector apparatus 40 is configured to correct the y offset and/or the y beam angle φ, orthogonal deflector apparatus 40 can be the same as second orthogonal deflector apparatus 240 discussed above. Of course, the order of first and second deflector apparatus 230, 240 can be switched in which case orthogonal deflector apparatus 40 as configured to correct the x offset and/or the x beam angle Θ can correspond to second orthogonal deflector apparatus 240 and orthogonal deflector apparatus 40 as configured to correct the y offset and/or the y beam angle φ can correspond to first orthogonal deflector apparatus 230.

One skilled in the art will also recognize that a pair (or more) of orthogonal deflector apparatus 40, 40' (e.g., corresponding to first and second deflector apparatus 230, 240 and/or x and y axes) can include intermingled or interleaved components. For example, the first orthogonal deflector 400 of deflector apparatus 40 can be disposed adjacent first orthogonal deflector 400' of deflector apparatus 40. Likewise, second orthogonal deflector 410 of deflector apparatus 40 can be disposed adjacent first orthogonal deflector 410' of deflector apparatus 40. In other words, the deflectors can be disposed as first orthogonal deflector 400 (corrects x offset) followed by first orthogonal deflector 400' (corrects y offset), followed by second orthogonal deflector 410 (corrects x beam angle Θ), followed by second orthogonal deflector 410' (corrects y beam angle φ). Of course, the deflectors can also be disposed in the opposite order: first orthogonal deflector 400' (corrects y offset) followed by first orthogonal deflector 400 (corrects x offset), followed by second orthogonal deflector 410' (corrects y beam angle φ), followed by second orthogonal deflector 410 (corrects x beam angle Θ). Those skilled in the art will recognize that other combinations and orders of the deflectors are possible.

In general, the deflectors 400, 410 can have a fast action and a predictable response with minimal hysteresis. For example, the deflectors 400, 410 can be designed to be as low in inductance as practical, and having laminated or ferrite return yokes.

Figure 5:
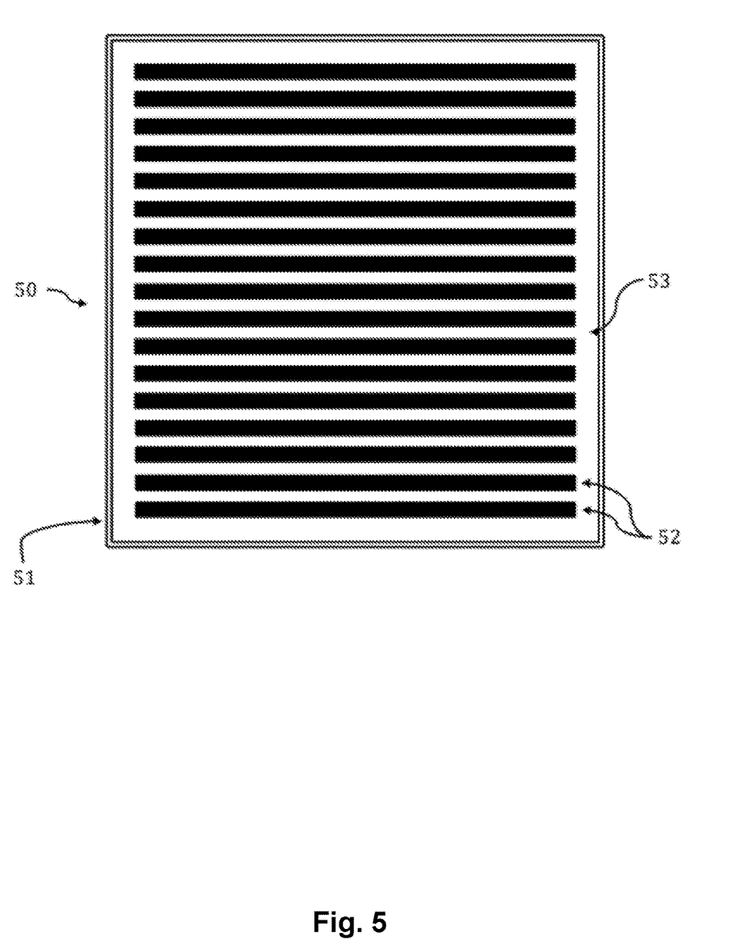
FIG. 5 illustrates a strip electrode assembly according to an embodiment.

FIG. 5 illustrates a strip electrode assembly 50 according to an embodiment. Strip electrode assembly 50 includes frame 51, film 53 and field strips 52. Assembly is performed by bonding tensioned film 53 to frame 51. Film 53 is aluminized polyimide and can have a thickness of about 25 mm or less in some embodiments (about 8.5 mm to about 12.5 mm, in one or more embodiments). However, other metalized polymers (e.g., Mylar, aluminum/gold/nickel coated polyimide/polyamide) can also be used. Frame 51 is made of aluminum or other suitable rigid material. As used herein, "about" means plus or minus 10% of the relevant value. It is noted that strip assembly 50 is provided to illustrate an exemplary embodiment of a PBS system.

As with all the disclosed electrode structures, vertical strip electrode assembly 50 is radiation resistant to prevent degradation. The electrode structures must also be as thin as possible to minimize scattering of the beam as it passes through the ionization chamber and energy loss in the detector. Field strips 52 are fabricated from pre-aluminized polymer film. In a preferred embodiment, the polymer is polyimide which is extremely radiation-resistant. The strength of polyimide also allows film 53 to be sufficiently thin (less than or equal to about 1000 A) and does not contribute significantly to beam scatter or energy loss.

The film 53 is stretched so it remains under tension during fabrication, and during use. The advantage of processing the film in its stretched state is that no distortion is added in post-processing. If the film were patterned then stretched, the pattern would be modified and the precision compromised.

The number of field strips 52 can range from 16 to 128, depending on spatial resolution. Field strips 52 are created by selectively removing the aluminum from film 53 to create a number of isolated electrodes on the insulating polymer substrate comprised by film 53. In one embodiment, the removal is performed using laser ablation. In this process, a highly-focused, nanosecond pulsed ultra-violet (UV) laser is directed onto the metal film surface. With sufficient energy density, the pulsed laser light vaporizes the metal film over an area of a few to tens of microns, leaving the substrate largely intact. The technique is capable of very high spatial accuracy, typically on the scale of a few microns. The process does not require mechanical contact with the film. Unlike alternative methods such as lithography, the material does not need to be coated, stripped, etched, etc., all of which can damage or distort the electrode film.

As part of the laser processing, alignment holes (not shown) are cut into film 53. These are precisely aligned with the electrode pattern. During the final assembly, these fiducial holes or markings are used to register film 53 with the support structure through the use of dowel pins. These same holes are then used to align the intermediate support structure with the overall support structure. In this way, the laser-ablated pattern can be aligned with the mechanical shell with an accuracy of less than or equal to about 10 microns.

Figure 6:
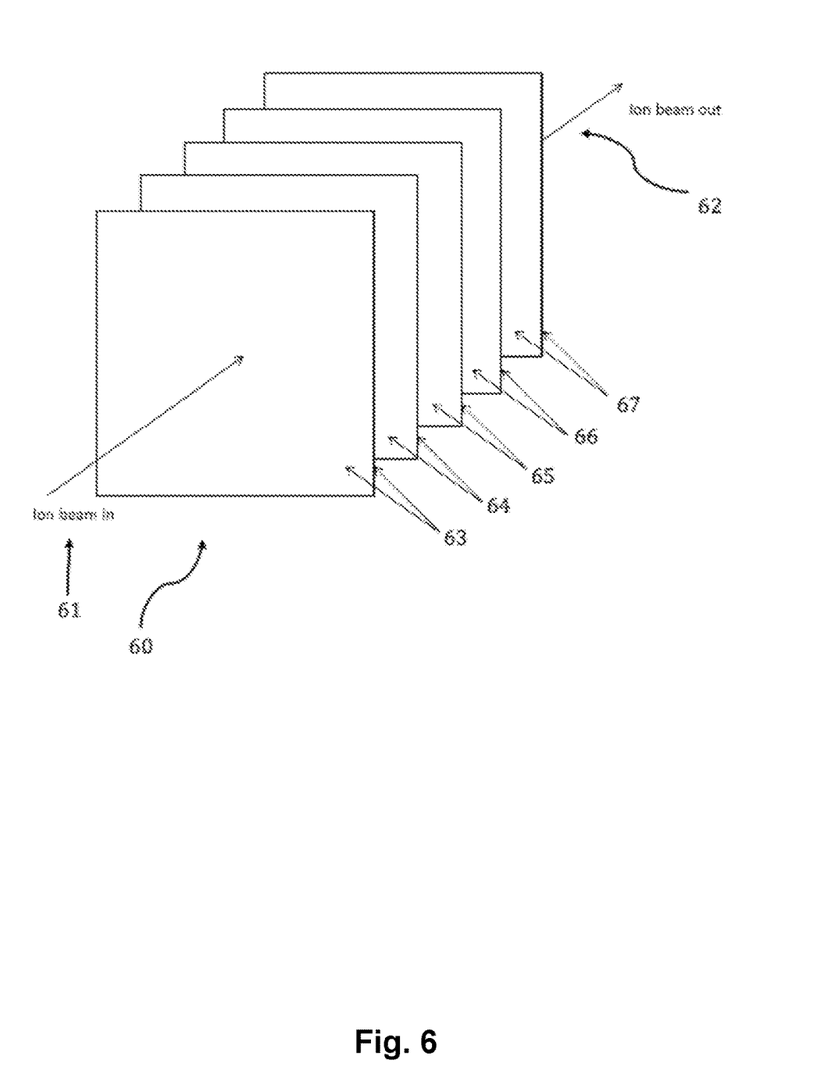
FIG. 6 illustrates an abstraction of a strip ionization chamber sub-assembly according to an embodiment.

FIG. 6 illustrates an abstraction of a strip ionization chamber sub-assembly 60 according to an embodiment. Ionization chamber sub-assembly 60 comprises ground planes 63, 67, high voltage (HV) planes 64, 66 and X-Y electrode plane 65. X-Y electrode plane 65 is a structure comprising X field strips and Y field strips, such as strip electrode 50 (in different orientations), on opposite sides, thereby minimizing the number of necessary electrode planes. HV planes are biased relative to X-Y plane thereby producing an electrostatic field with field lines similar to that of a parallel plate capacitor. In operation, particle beam 61 ingresses ionization chamber sub-assembly 60 through ground plane 63.

A gas gap disposed between HV plane 64 and X-Y plane 65 gives rise to an active region associated with an ionization event. Gas molecules in the active region become ionized after being struck by particle beam 61. Consequently, cations are pulled toward the HV 64 which acts as the cathode. Conversely, anions are drawn into X-Y electrode plane 65 (anode), pursuant to the Lorentz force albeit with thousands of small scattering events which limit velocity.

In some embodiments, HV plane 64 is biased with a positive voltage and thus acts as the anode, which collects electrons and negative ions. The X-Y electrode plane 65 is grounded and acts as the cathode, which collects positive ions.

Similarly, a gas gap disposed between HV plane 66 and X-Y electrode plane 65 gives rise to an additional active region. Gas molecules in the active region become ionized after being struck by particle beam 61, after passing through X-Y electrode plane 65. Subsequently, cations are pulled toward the HV 66 which acts as the cathode. Conversely, anions are drawn toward X-Y electrode plane 65 (anode). Particle beam 62 egresses ionization chamber sub-assembly 60 through ground plane 67.

In some embodiments, HV plane 66 is biased with a positive voltage and thus acts as the anode, which collects electrons and negative ions. The X-Y electrode plane 65 is grounded and acts as the cathode, which collects positive ions.

HV planes 64, 66 are made from unpatterned metalized polyimide, although they may be made from any suitably radiative resistant material (rad hard) exhibiting bulk conductivity. In an alternate embodiment, a single, two-sided HV plane replaces the X-Y electrode plane 65 and vertical and horizontal electrodes (faced accordingly) replace HV planes 64, 66.

The strip electrode assembly 50 and/or the strip ionization chamber sub-assembly 60 can be used in system 20 or method 30, such as in first and/or second detector apparatus 250, 260 discussed above. Strip electrode assembly 50 and strip ionization chamber sub-assembly 60 are further described in U.S. patent application Ser. No. 14/215,311, which is hereby incorporated by reference, as discussed above. One skilled in the art will recognize that additional configurations of the PBS system are possible in system 20 and/or method 30, including different ionization chambers than those described herein or replacing the disclosed ionization chambers with other position-sensitive detectors.

Figure 7:
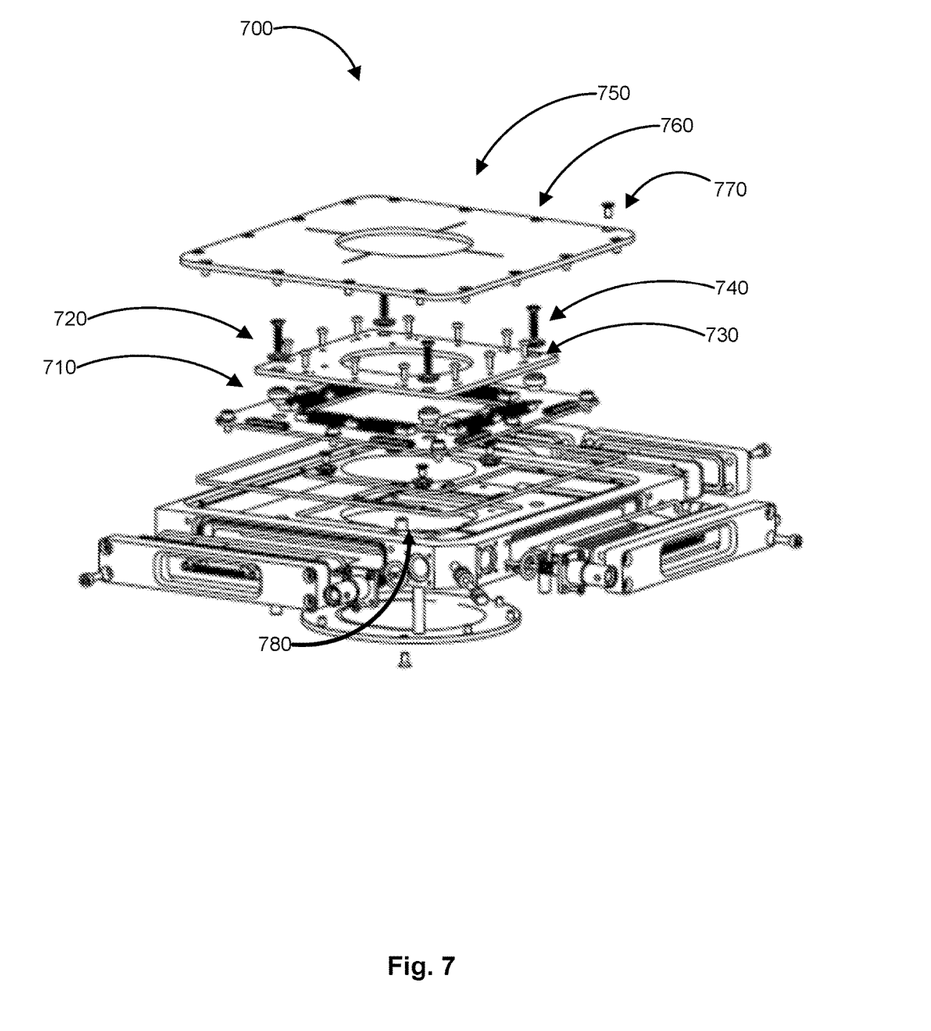
FIG. 7 illustrates an exploded perspective view of a pixelated detector according to an embodiment.

FIG. 7 illustrates an exploded perspective view of a pixelated detector 700 according to an embodiment. The detector 700 includes an ablated (or pixelated) electrode material 710 bonded to a support plate 720. The support plate 720 can be a rigid insulating substrate, such as FR4 fiberglass, or a metal plate (e.g., nickel-plated aluminum), depending on the need to maintain electrical isolation on the bonded surface. The support plate 720 can be mounted on the ablated electrode material 710 utilizing fiducial structures 730 and alignment pins 740 to provide mechanical alignment between the ablated pattern and the support plate 720, which can provide an accuracy greater than about 25 microns.

The support plate 720 is disposed in an instrument case 750 using fiducial structures 760 and dowel pins 770 to maintain a high degree of mechanical alignment between the electrode pattern 710 and the instrument case 750.

A bias electrode 780 is fabricated in a similar manner, without the need for any patterning. The bias electrode 780 is mounted in the instrument case 750 with high-precision spacers to maintain a stable and accurate gas layer between the two electrode layers. The gas layer can include or can be air.

Figure 8:
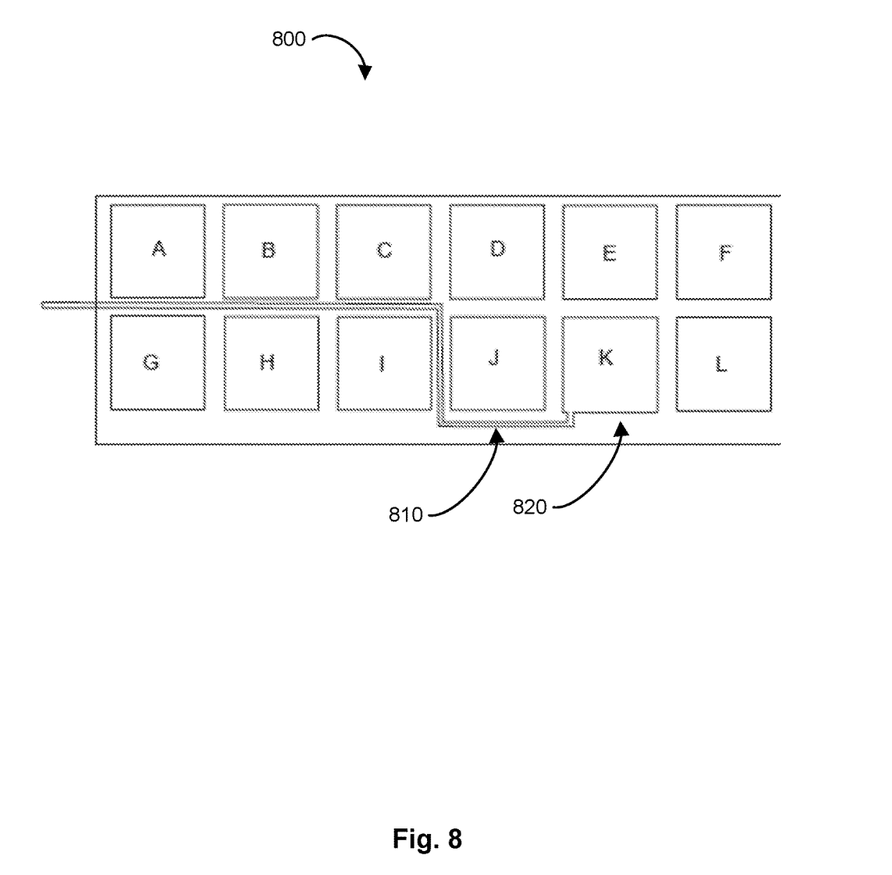
FIG. 8 illustrates an array of pixels according to an embodiment.

FIG. 8 illustrates an array of pixels 800 according to an embodiment. The array of pixels 800 can be disposed in ablated electrode material 710. For illustration purposes, a front side trace 810 for a single pixel (K) 820 is shown for clarity. Back side traces are also possible using plated through holes to connect the pixel to the trace.

The pixelated detector 700 and/or the pixel array 800 can be used in system 20 or method 30, such as in first and/or second detector apparatus 250, 260 discussed above. Pixelated detector 700 and/or Pixel array 800 are further described in U.S. patent application Ser. No. 14/493,098, which is hereby incorporated by reference, as discussed above.

Figure 9:
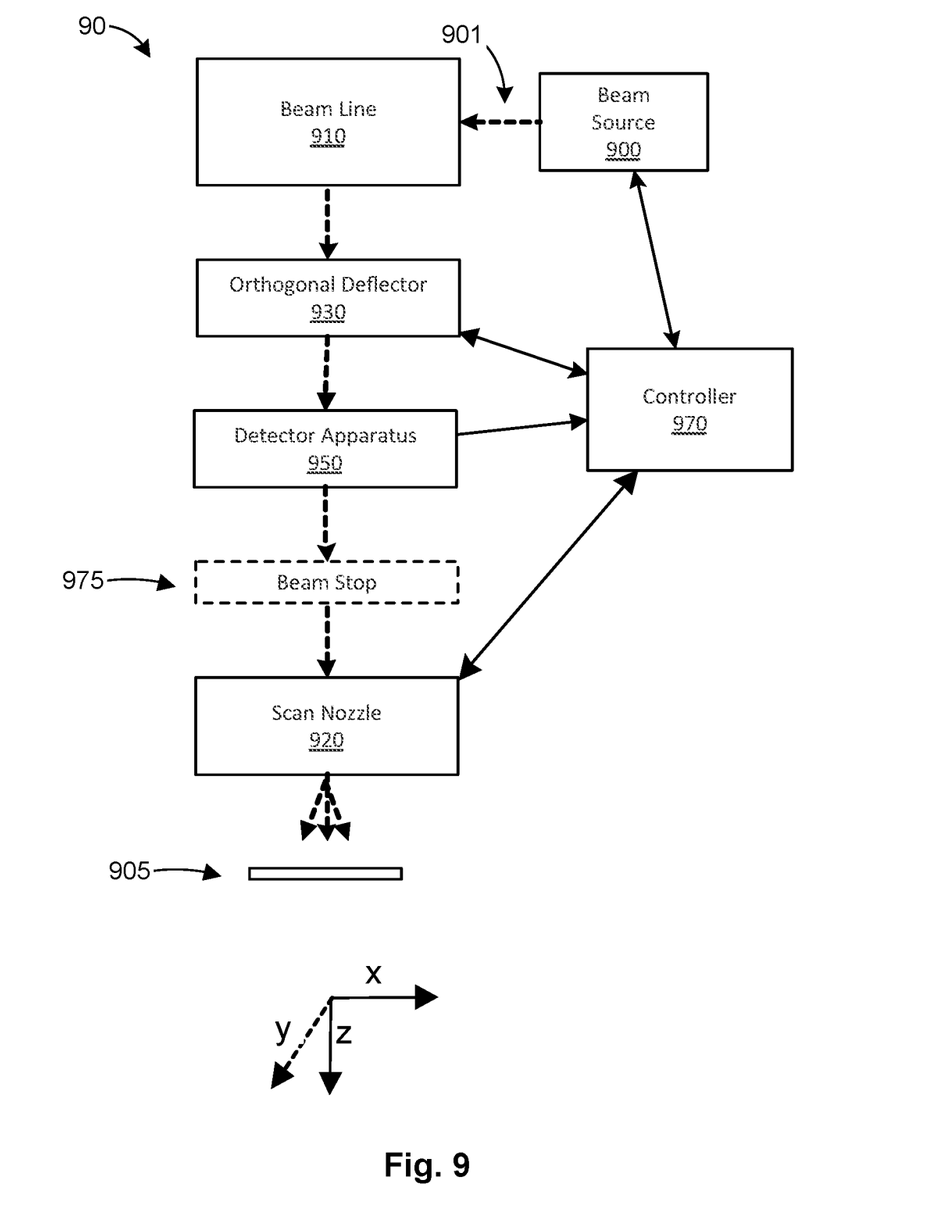
FIG. 9 illustrates a pencil beam system according to an embodiment.

FIG. 9 illustrates a PBS system 90 according to an embodiment. The system 90 includes beam source 900, beam line 910, orthogonal deflector 930, detector apparatus 950, controller 970, and optional beam stop 975. Beam source 900 and beamline 910 can be the same as or different than beam source 100/200 and beamline 110/210 described above. Isocenter plane 905 is illustrated for reference.

PBS system 90 is a simplified embodiment of PBS system 20 described above. In PBS system 90, only the offset correction parameters are controlled by controller 970.

Detector apparatus 950 measures the two-dimensional position (e.g., (x, y) position) of beam 901, similar to first and second detector apparatus 250, 260 discussed above. For example, detector apparatus 950 can include a pixelated detector or a pair of strip detectors. Controller 970 compares the measured x and y positions of beam 901 with model x and y positions of a model beam to determine an offset error, as described above. Controller 970 then generates a control signal to correct the x and/or y components of the offset error. The control signal is sent to orthogonal deflector 930.

Orthogonal deflector 930 generates magnetic fields to adjust the trajectory of beam 901. Orthogonal deflector 930 can independently adjust the x and y components of beam 901 trajectory. For example, orthogonal deflector 930 can include a first pair of correction magnets to adjust the x component of beam 901 trajectory and a second pair of correction magnets to adjust the y component of beam 901 trajectory. Each pair of correction magnets can be the same as orthogonal deflectors 400 or orthogonal deflectors 410 discussed above. Alternatively, orthogonal deflector 930 includes a multipole electromagnet that provides a combined function of correcting the x and y components of beam 901 trajectory.

After passing through orthogonal deflector 930, the trajectory of beam 901 is corrected to compensate for the measured offset error. It is recognized that the beam angle will have to be adjusted to correct the measured offset error of beam 901.

As can now be appreciated, the present disclosure provides improved control systems and methods for controlling a charged particle pencil beam system. The control system includes first and second ionization chambers to detect the position and beam angle of the beam at two locations along the beam path. The measured position and beam angle are compared with a model position and beam angle to determine an offset error and a beam angle error in the beam. A first pair of orthogonal correctional magnets is used to modify the beam path to reduce the "x" component of the offset and beam angle errors. A second pair of orthogonal correctional magnets is used to modify the beam path to reduce the "y" component of the offset and beam angle errors. Thus, the control system provides up to four degrees of freedom to control the beam in real time during therapy.

The present invention should not be considered limited to the particular embodiments described above, but rather should be understood to cover all aspects of the invention as fairly set out in the present claims. Various modifications, equivalent processes, as well as numerous structures to which the present invention may be applicable, will be readily apparent to those skilled in the art to which the present invention is directed upon review of the present disclosure. The claims are intended to cover such modifications.

What is claimed is:

1. A system for providing real-time trajectory correction of a charged particle beam, comprising:
   a particle beam generator to generate a generated particle beam parallel to a reference axis;
   a transport beamline apparatus comprising beamline deflector magnets to generate magnetic fields to deflect said generated particle beam along a defined trajectory towards a scan nozzle;
   a scan nozzle comprising at least one scan magnet to direct said deflected particle beam to a target position in a patient;
   a first detector apparatus disposed between said transport beam apparatus and said scan nozzle, said first detector apparatus configured to output a first signal representing a first measured position of said deflected particle beam in orthogonal first and second planes, wherein said reference axis lies on said first and second planes;
   a second detector apparatus disposed between said first detector apparatus and said scan nozzle, said second detector apparatus configured to output a second signal representing a second measured position of said deflected particle beam in said first and second planes;
   a pair of first correction magnets disposed between said first detector apparatus and said particle beam generator, said first correction magnets configured to (a) receive from a control system an offset control signal and a beam angle control signal and (b) generate magnetic fields to correct a measured offset error and a measured beam angle error with respect to said first plane; and
   a pair of second correction magnets disposed between said first detector apparatus and said particle beam generator, said second correction magnets configured to (a) receive from said control system an offset control signal and a beam angle control signal and (b) generate magnetic fields to correct said measured offset error and said measured beam angle error with respect to said second plane;
   wherein said control system comprises a processor, said control system configured to:
      receive as inputs said first and second signals;
      calculate a measured trajectory of said deflected particle beam based on said first and second measured positions, said measured trajectory including a measured beam angle and a measured offset;
      determine said measured beam angle error based on said measured beam angle and a model beam angle of said generated particle beam;
      determine said measured offset error based on (a) at least one of said measured offset, said first measured position, or said second measured position and (b) a corresponding model position of said generated particle beam;
      generate said beam angle control signal based on said measured beam angle error; and
      generate said offset control signal based on said measured offset error.

2. The system of claim 1, wherein said first pair of correction magnets includes a first magnet configured to correct said deflected offset of said deflected particle beam in said first plane and a second magnet configured to correct said deflected beam angle of said deflected particle beam in said first plane.

3. The system of claim 2, wherein said first magnet is configured to deflect said deflected particle beam at a first angle to compensate for said measured offset error in said first plane as the beam travels from said first magnet to said second magnet.

4. The system of claim 3, wherein said second magnet is configured to deflect said deflected particle beam at a second angle to compensate for said measured beam angle error in said first plane.

5. The system of claim 1, wherein said second pair of correction magnets includes a first magnet configured to correct said deflected offset of said deflected particle beam in said second plane and a second magnet configured to correct said deflected beam angle of said deflected particle beam in said second plane.

6. The system of claim 5, wherein said first magnet is configured to deflect said deflected particle beam at a first angle to compensate for said measured offset error in said second plane as the beam travels from said first magnet to said second magnet.

7. The system of claim 6, wherein said second magnet is configured to deflect said deflected particle beam at a second angle to compensate for said measured beam angle error in said second plane.

8. The system of claim 5, wherein said second pair of correction magnets includes (a) a first magnet pair that includes the first magnet and a first opposing magnet, the first magnet and the first opposing magnet disposed along a first axis that lies on the second plane, the first axis orthogonal to the reference axis, and (b) a second magnet pair that includes the second magnet and a second opposing magnet, the second magnet and the second opposing magnet disposed along a second axis that lies on the second plane, the second axis orthogonal to the reference axis and parallel to the first axis.

9. The system of claim 1, wherein said measured beam angle error includes a first measured beam angle error with respect to said first plane and a second measured beam angle error with respect to said second plane.

10. The system of claim 1, wherein said measured offset error includes a first measured offset error with respect to said first plane and a second measured offset error with respect to said second plane.

11. The system of claim 1, further comprising a beam stop disposed between said pair of second correction magnets and said scan nozzle.

12. The system of claim 1, wherein said control system is configured to iteratively adjust said deflected offset and said deflected trajectory.

13. The system of claim 1, wherein said pair of first correction magnets and said pair of second correction magnets are disposed between said first detector apparatus and said transport beamline apparatus.

14. The system of claim 1, wherein said first detector apparatus includes a first strip detector configured to measure said first measured position in said first plane and a second strip detector configured to measure said first measured position in said second plane.

15. The system of claim 1, wherein said first detector apparatus includes a pixelated detector comprising orthogonal detector elements for measuring said first measured position in said first and second planes.

16. A system for providing real-time trajectory correction of a charged particle beam, comprising:
- a particle beam generator to generate a generated particle beam parallel to a reference axis;
- a transport beamline apparatus comprising beamline deflector magnets to generate magnetic fields to deflect said generated particle beam along a defined trajectory towards a scan nozzle;
- a scan nozzle comprising at least one scan magnet to direct said deflected particle beam to a target position in a patient;
- a detector apparatus disposed between said transport beam apparatus and said scan nozzle, said detector apparatus configured to output a measured position signal representing a first measured position of said deflected particle beam in orthogonal first and second planes, wherein said reference axis lies on said first and second planes;
- a correction electromagnet apparatus disposed between said detector apparatus and said particle beam generator, said correction electromagnetic apparatus configured to (a) receive from a control system an offset control signal and (b) generate magnetic fields to correct a measured offset error;

wherein said control system comprises a processor, said control system configured to:
- receive as an inputs said measured position signal;
- determine said measured offset error based on said first measured position and a model position of said generated particle beam; and
- generate said offset control signal based on said measured offset error.

17. The system of claim 16, wherein said detector apparatus includes a first strip detector configured to measure said first measured position in said first plane and a second strip detector configured to measure said measured position in said second plane.

18. The system of claim 16, wherein said detector apparatus includes a pixelated detector comprising orthogonal detector elements for measuring said first measured position in said first and second planes.

19. The system of claim 16, wherein said correction electromagnet apparatus includes a multipole electromagnet.

20. The system of claim 16, wherein said correction electromagnet apparatus includes first and second correction electromagnets, said first correction electromagnet configured to generate a first magnetic field to correct said measured offset error with respect to said first plane, said second correction electromagnet configured to generate a second magnetic field to correct said measured offset error with respect to said second plane.

* * * * *